United States Patent [19]

Ogilvie

[11] Patent Number: 4,508,898

[45] Date of Patent: Apr. 2, 1985

[54] ANTIVIRAL TRIAZINE COMPOUNDS

[76] Inventor: Kelvin K. Ogilvie, 54, Place de Bretagne, Candiac, Quebec, Canada, J5R 3M8

[21] Appl. No.: 386,430

[22] Filed: Jun. 8, 1982

Related U.S. Application Data

[63] Continuation-in-part of Ser. No. 302,790, Sep. 16, 1981, which is a continuation-in-part of Ser. No. 187,631, Sep. 16, 1980, Pat. No. 4,347,360.

[51] Int. Cl.³ .................. C07D 251/10; C07D 251/46
[52] U.S. Cl. ................................ 544/211; 544/194
[58] Field of Search ............ 544/298, 309, 313, 194, 544/211

[56] References Cited

U.S. PATENT DOCUMENTS

| | | | |
|---|---|---|---|
| 4,146,715 | 3/1979 | Schaeffer | 544/276 |
| 4,171,431 | 10/1979 | Skulnick | 544/194 |
| 4,199,574 | 4/1980 | Schaeffer | 424/200 |
| 4,347,360 | 8/1982 | Ogilvie | 544/276 |
| 4,355,032 | 10/1982 | Verheyden et al. | 424/253 |

FOREIGN PATENT DOCUMENTS 0049072  4/1982  European Pat. Off. ............ 544/276

Primary Examiner—Donald G. Daus
Assistant Examiner—S. A. Gibson
Attorney, Agent, or Firm—Fleit, Jacobson, Cohn & Price

[57] ABSTRACT

Compounds to general formula

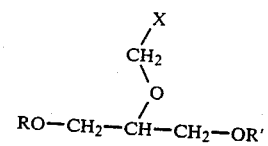

in which R and R' are hydrogen or benzyl and X represents a purine on pyrimidine base group selected from isoguanine, guanine, cytosine, 5-fluorouracil, S-methyl uracil (thymine) and chloroguanine, exhibit anti-viral properties.

1 Claim, No Drawings

4,508,898

ANTIVIRAL TRIAZINE COMPOUNDS

CROSS REFERENCE TO RELATED APPLICATION

This is a continuation-in-part of application Ser. No. 302,790, filed Sept. 16, 1981, which in turn is a continuation-in-part of application Ser. No. 187,631 filed Sept. 16, 1980 now U.S. Pat. No. 4,347,360.

BACKGROUND OF THE INVENTION

This invention relates to a novel process for the preparation of ring-open nucleoside and nucleotide analogues and the like and certain novel ring-open nucleoside analogues which show bioregulation activity.

BRIEF REFERENCE TO THE PRIOR ART

Nucleosides comprise a D-ribose or 2-deoxy-D-ribose sugar unit, chemically bonded to a purine or pyrimidine base selected from adenine, cytosine, guanine, thymine and uracil, via a nuclear nitrogen atom of the base. Since they are units of nucleic acids found naturally in living cells it has been speculated previously that nucleosides and nucleotides and their related analogues might have potential as chemotherapeutic agents. An example of a compound disclosed in the prior art as useful in antiviral treatments is acycloguanosine (acyclovir), described in U.S. Pat. No. 4,146,715 Schaeffer.

SUMMARY OF THE INVENTION

The present invention relates to antivirally active nucleoside analogues, processes for their preparation and pharmaceutically acceptable compositions thereof for administration to mammals to treat viral infections. The nucleoside analogues of the present invention are N-substituted purine and pyrimidine compounds corresponding to the general formula:

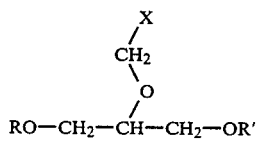

wherein X represents a uracil group, optionally substituted at its 5-position with halogen or lower alkyl, a cytosine group, a 5-azacytosine group, a 6-halo-substituted guanine group or an isoguanine group, and R and R' are independently selected from hydrogen and benzyl.

It will be appreciated that the compounds according to the present invention are closely analogous in structure and groupings to naturally occurring nucleosides. The essential chain arrangements and lengths are maintained. The appropriate O and OH functional groups, which in biological environments actively bind to biological centers, are maintained in their natural sequences and disposition relative to the base, but optionally modified with "protecting" groups. Indeed, the groups adjacent to the bases are so similar in chemical constitution to deoxyribose compounds that they can assume the essential conformation of the deoxyribose ring under appropriate conditions. The fundamental difference is that the compounds of the present invention lack the structural rigidity of carbohydrate ring, which renders them unpredictably different in properties and behaviour. Also, the C-4' position is not chiral, in compounds of formula I, so that stereoisomers do not arise. Each hydroxyl is primary. There can be no syn-anti isomerism about the glycosidic bond.

Compounds of general formula I may be made by coupling the appropriately halogenated base with the appropriate alkyl residue. The synthesis may be initiated by treating 1,3-dichloro-2-propanol with sodium benzylate under a nitrogen atmosphere followed by trioxymethylene and HCl to prepare the chloromethoxy derivative of 1,3-dibenzyloxy-2-propanol, care being taken to remove excess water. This derivative may be coupled to the appropriately halogenated base, such as 6-chloropurine, in DMF using triethylamine as acid scavenger. Treatment of the chloro compound so formed with methanolic ammonia in a steel reaction bomb gives the 6-amino derivative.

The product may be debenzylated to give a hydroxyl compound of formula I eg. with hydrogen over palladium oxide in methanol. Protecting groups, if desired, are put on by standard known methods. Alternatively halogenated alkyl residues may be coupled with halogenated or non-halogenated purine or pyrimidine base compounds. It is preferred to use the non-halogenated base compounds, e.g. guanine, as the starting material, since this is a very cheap, readily available material. Instead of halogens, chlorine, bromine, iodine or fluorine as the leaving group, one may use substituted silyl, lower alkyl or a salt of a metal selected from mercury, silver or tin.

In preparing dihydroxy side chain compounds of the present invention, it is preferred to use the corresponding dibenzyloxy compounds as intermediates or starting materials. The dibenzyloxy compounds can be debenzylated to yield the dihydroxay compounds quite readily, for example by catalytic transfer hydrogenation with palladium black and cyclohexene, or by Birch reduction. The dibenzyloxy compounds may be prepared as described above, by coupling to the purine or pyrimidine base compound a halomethoxy derivative of 1,3-dibenzyloxy-2-propanol.

Several of the compounds of the present invention show anti-viral activity, accompanied by low cell toxicity, rendering them potentially useful in therapeutic compositions to combat specific viral invaders of living mammalian cells. For example, the compound 9-[[2-hydroxy-1-(hydroxymethyl)ethoxy]methyl] cytosine exhibits activity against herpes simplex virus. Certain compounds of the aforementioned formula I in which the purine or pyrimidine base group X is substituted on the nucleus are also of interest as potential anti-viral agents. For example, the compound 9-[[2-benzyloxy-1-(benzyloxymethyl)ethoxy]methyl]-6-chloroguanine has shown significant activity against coxsackievirus B3. The compound 1-[[2-benzyloxy-1-(benzyloxymethyl)ethoxy]methyl]-5-methyluracil is active against vesicular stomatitis virus. The present applicant has described and claimed elsewhere (see aforementioned U.S. application Ser. No. 187,631) the compound 9-[[hydroxy-1-(hydroxymethyl)ethoxy]methyl]guanine, also referred to as G*, and its activity against herpes virus of different types. The present invention provides new and improved methods of synthesis applicable to G*.

It will of course be understood that the present invention extends to cover pharmaceutically acceptable salts of the compounds described herein. The compounds are active to combat, prevent or at least substantially inhibit the replication of the viruses, at a dosage level at which they are non-toxic to mammalian cells.

Compounds according to the present invention may be administered to a patient parenterally, interthecally applied topically as ointment, cream, aerosol or powder, or even on occasion given as eye or nose drops or orally. In general, methods of administration and dosage formulations thereof follow the known, published methods used with known antiviral drugs such as acycloguanosine, Ara-A and Ivdr. Effective unit doses for administration of the compositions interthecally or parenterally, calculated as free base, are suitably in the range from about 0.1–100 mg per kg mammal body weight, most suitably in the 0.5–20 mg per kg mammal body weight, and most preferably about 5 mg per kg, on the basis of a dosage administered from 2–4 times per day.

Orally administrable compositions are preferably in fine powder or granule form, with diluting and/or dispersing and/or surface active agents, e.g. in water or in a syrup dispersion, or as tablets or capsules. Solutions of the compounds in distilled water or saline, e.g. isotonic solutions and optionally buffered with phosphate, of concentration 1–20% preferably 2–15% and most preferably around 10%, are suitable for parenteral or interthecal administration. Ointments (topical or cream) may be compounded for treatment of external infections, e.g. with an oil-in-water cream base, in a concentration of from about 0.1–10%, preferably up to about 3%, most preferably about 1% w/v active ingredient. They may be compounded with paraffin oil, with petrolatum to form emulsion optionally with a surfactant for stabilizing purposes, or with dimethyl-sulfoxide.

The invention is further illustrated in the following non-limitative examples.

EXAMPLE 1

Dibenzylchloro-G*

6-Chloroguanine (200 g, 0.11 moles), HMDS (200 ml) and ammonium sulfate (300 mg) were combined and brought to reflux with stirring. After 1.75 h more ammonium sulfate was added. After a further hour the mixture was clear. The excess 1,1,1,3,3,3-hexamethyldisilazane (HMDS) was distilled under reduced pressure to yield a solid. The solid was dissolved in dry benzene (200 ml), mercuric cyanide (34 g, 0.135 moles) was added and stock 1,3-dibenzyloxy-2-chloromethoxy propane (0.110 moles) was added. The stirred mixture was brought to reflux. Reflux was continued for 5 hours. The mixture was cooled and filtered and the residue was washed with benzene. The filtrate, and washings were combined and evaporated under reduced pressure to yield a syrup. The syrup was dissolved in methylene chloride (400 ml) and washed successively with water (400 ml), 30% aqueous potassium iodide (4×200 ml), water (200 ml) and aqueous bicarbonate (2×200 ml). The methylene chloride phase was dried with sodium sulfate and evaporated to yield 54 g of syrup. The rest of the syrup was dissolved in chloroform (50 ml) and applied to a prep. silica column (19.5×6.3 cm). The column was eluted with 1% methanol in chloroform and fractions were collected. The desired material, namely 9-[[2-benzyloxy-1-(benzyloxymethyl)ethoxy]methyl]-6-chloroguanine, of formula

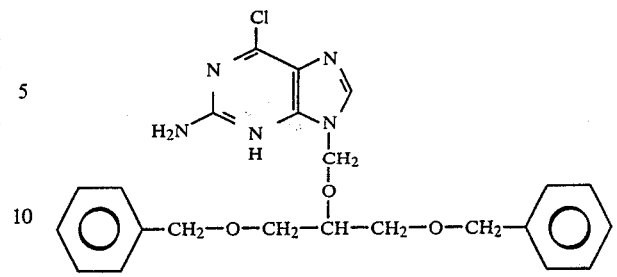

was isolated from the appropriate fractions issuing from the column.

EXAMPLE 2

Preparation of 9-[[2-hydroxy-1-(hydroxymethyl)ethoxy]methyl]guanine (G*)

Guanine (1.51 g, 0.01 m) and ammonium sulfate (300 mg) were suspended in HMDS (40 ml) and brought to reflux with stirring. After 2 days of reflux and the occasional addition of ammonium sulfate the mixture became clear. The excess HMDS was removed under reduced pressure and the residue was dissolved in benzene (40 ml). Mercuric cyanide (3 g, 0.012 m) was added followed by the addition of 1,3-dibenzyloxy-2-chloromethoxy propane (0.01 m). The mixture was refluxed for 5 hours. The mixture was diluted with chlorofrom (200 ml) and washed successively with water, 30% aqueous potassium iodide (3×) and water. The organic phase was dried with anhydrous sodium sulfate and evaporated under reduced pressure to yield a syrup (5.8 g). The syrup was mixed with ethanol (150 ml), heated and allowed to stand. Filtration gave 1.5 g of crystals, which by NMR spectroscopic analysis proved to be a mixture of 9-[[2-benzyloxy-1-(benzyloxymethyl)]ethoxymethyl]guanine and 7-[[2-benzyloxy-1-(benzyloxymethyl)]ethoxymethyl]guanine. The mixture components were separated on a column or by selective crystalization, and then the 9-substituted guanine was dissolved in refluxing ethanol (500 ml). Then, to effect debenzylation thereof, cyclohexene (400 ml) was added followed by the addition of palladium black (previously used, estimated amount was about 15 g); after 15 hours the debenzylation reaction was judged (t.l.c.) to be complete. The mixture was cooled a little and filtered. The filtrate was evaporated under reduced pressure and it yielded less than 1 gram of residue. The palladium catalyst residue was suspended in dimethyl formamide, heated on a boiling water bath and then filtered. This procedure was repeated another 4 times and two hot methanol washings were also performed. All of the washings were combined and evaporated under reduced pressure. The residue was dissolved in hot water-ethanol and filtered through celite containing activated charcoal. The filtrate was evaporated under reduced pressure. The solid residue was recrystallized from hot water-ethanol. The crystals were filtered and washed with ethanol. The mother liquor was evaporated under reduced pressure. The residue was dissolved in hot water-ethanol and set aside to crystallize. The crystals were filtered and washed with ethanol. NMR. spectroscopy confirmed that the product was G* ie. 9-[[2-hydroxy-1-(hydroxymethyl)ethoxy]methyl]guanine with the structural formula:

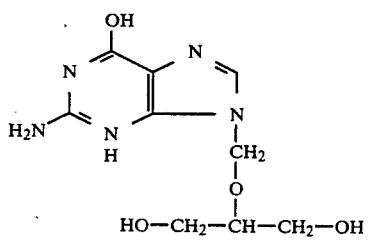

EXAMPLE 3

In this Example, the dibenzyl-chloro guanine compound, as produced in Example 1, was dechlorinated and then de-benzylated by Birch reduction, to produce the compound G* as shown above in Example 2.

A sample of the compound II (69 g), as shown in Example 1, methanol (360 ml). Mercapto ethanol (12 ml) and weter (1.5 ml) were added followed by 1N sodium methoxide solutions (160 ml) and the mixture was brought to reflux. A thio-intermediate is formed within about 0.5 hours. Continued heating for 4.5 hours converts most of the thio-intermediate to the desired dechlorinated compound of formula:

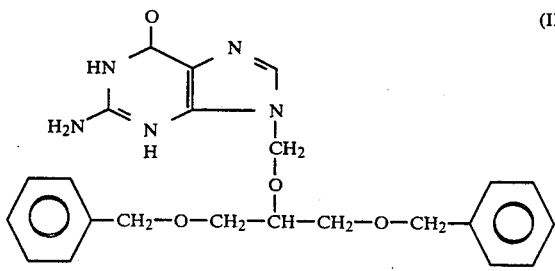

(III)

A two-liter three-necked flask fitted with a dry ice condensor was cooled in an acetone-dry ice bath under a stream of nitrogen. About one liter of liquid ammonia was collected in the flask by condensing dry ammonia gas. A slurry of the compound III (20 g, 45.7 mmole) in dry THF (100 ml) was added with stirring. The temperature of the bath was then allowed to rise to −45° to −40° C. Sodium was then added in small quantities until a permanent blue colour was obtained. The stirring was continued for 15 minutes. The blue colour was then discharged by the addition of ammonium chloride in small quantities (Note: All the above operations were carried out under nitrogen). The ammonia and THF were then evaporated off under a stream of nitrogen. The white residue obtained was agitated with benzene (300 ml) and filtered The solid left behind was dissolved in water (500 ml) and extracted with benzene (3×200 ml). The aqueous layer was acidified with acetic acid Ph 5-6 and left overnight. The white precipitate obtained was collected by filtration. It was dissolved in boiling water (700 ml). Charcoal (neutral) was then added and the mixture filtered. The filtrate on standing gave 7.6 g of white crystals. The mother liquors on concentration yielded another crop of crystals (1.4 g). The compound was identified as G*, of structural formula as shown in Example 2.

EXAMPLE 4

Preparation of 9-[[2-hydroxy-1-(hydroxymethyl)ethoxy]methyl]-isoguanine

Isoguanine sulfate 49 (4.5 g, 0.018 mole) was suspended in HMDS (100 ml) with ammonium sulfate (300 mg) and brought to reflux. After 1 hour the mixture was clear and the excess HMDS was removed under reduced pressure to yield a syrup. The syrup was dissolved in benzene (100 ml), followed by the addition of mercuric cyanide (6.3 g) and stock chloride 3 (15.5 mole). The stirred mixture was refluxed for 1½ hours. The volume was reduced to 50 ml, poured into water (400 ml) and diluted with chloroform (500 ml). After shaking, the phases were separated with a precipitate present in the chloroform phase. The chloroform phase was shaken with 30% aqueous potassium iodide but the precipitate persisted. The mixture was filtered through celite and the phases were separated. The chloroform phase was washed twice with 30% aqueous potassium iodide and once with water. The chloroform phase was dried with anhydrous sodium sulfate and evaporated under reduced pressure to yield about 5 g of syrup. The syrup was dissolved in chloroform (10 ml) and applied to a tlc silica column (12×6.3 cm). The column was eluted with 2% methanol in chloroform. From fraction thus recovered, there was isolated 2.72 g of a compound which was characterized as 9-[[2-benzyloxy-1-(benzyloxymethyl)-ethoxy]methyl]isoguanine of structural formula:

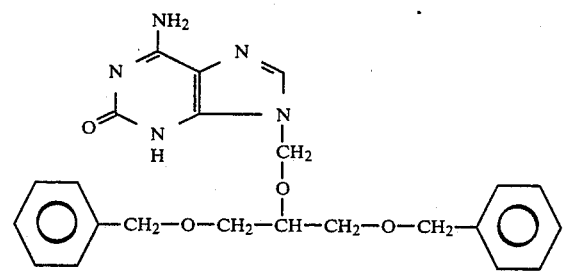

In order to prepare from this the dihydroxy derivative, 1.1 g of compound III was dissolved in ethanol (40 ml) and cyclohexene (20 ml). Then palladium oxide (1 g) was added and the mixture was refluxed for 2 hours when the reaction was judged complete by tlc. The mixture was filtered and the residue was washed with hot ethanol. The filtrate was evaporated under reduced pressure to yield a syrup. The syrup was dissolved in a mixture of water (1.5 ml) and ethanol (5 ml). Then about 30 ml of ethanol was added and a precipitate formed. The precipitate was filtered and the precipitate did not move from the origin on tlc using 60% MeOH in CHCl₃. The filtrate was evaporated to yield 0.51 g of amorphous gum, determined to have the structural formula

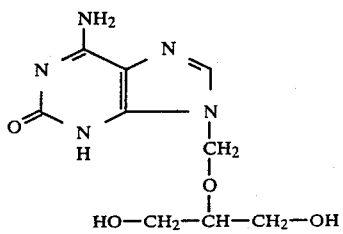

9-[[2-hydroxy-1-(hydroxymethyl)ethoxy]methyl-]isoguanine, iso G*.

EXAMPLE 5

Preparation of 1-[[2-benzyloxy-1-(hydroxymethyl)ethoxy]methyl]-5-fluorouracil

1-[[2-benzyloxy-1-(benzyloxymethyl)ethoxy]methyl]-5-fluorouracil, prepared by the method described in Example 5 of parent U.S. application Ser. No. 187,631, was used as the starting material. Essentially the method involves reaction of 5-fluorouracil with 1,3-dibenzyloxy 2-chloromethoxy propane in the presence of HMDS. 8.325 g of the starting material was dissolved in normal ethanol. Used palladium oxide (8.3 g) was added followed by cyclohexene (125 ml). The stirred mixture was brought to reflux and after 3 hours the reaction was judged (tlc) to be complete. The reaction mixture was filtered and the residue was washed with warm ethanol. The filtrate and washings were combined and evaporated to yield 6.4 g of syrup. The syrup was dissolved in hot ethanol (11 ml) and seeded with a few crystals. There was obtained from the liquor by crystallization and filtration about 3.76 g of crystals of 5-fluoro-1-[[-hydroxy-1-(hydroxymethyl)ethoxy]methyl]uracil—see aforementioned U.S. application Ser. No. 187,631. The mother liquor was evaporated and applied to 8 prep. tlc plates and developed with 10% methanol in chloroform. The fastest component was scraped off which after extraction with acetone yielded about 20 mg of compound 16. The plates were then developed with acetone. The faster running zone after scraping and extraction with acetone gave about 0.17 g of material whose NMR spectrum indicated that it was the monobenzyl compound of formula

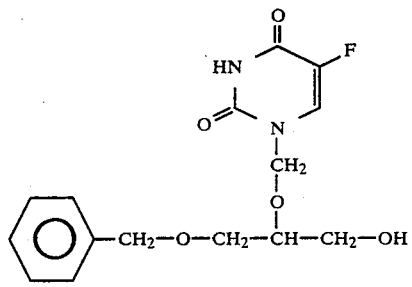

monobenzyl-5 FU*

The compound was further purified by application to two prep. tlc plates and development with 10% methanol in chloroform. The zone was extracted with acetone and evaporated to yield 100 mg of syrup, analysis of which showed a product in conformity with formula V above.

EXAMPLE 6

Preparation of 1-[2-benzyloxy-1-(benzyloxymethyl)ethoxy]-5-methyluracil (or, 1-bis-(benzyloxymethyl)methoxymethylthymine Thymine (2.5 g) and triethylamine (TEA, 2.04 g) were dissolved in "dry" dimethylformamide (D.M.F., 50 ml). 1,3-dibenzyloxy-2-chloromethoxy propane (compound 50, 6.4 g) was then added and the reaction mixture was stirred at 22° C. for 2 days. Upon addition of the 1,3-dibenzyloxy-2-chloromethoxy propane, TEA. HCL immediately began to precipitate. The DMF solution was then cooled to −20° C., filtered and concentrated to a thick syrup which was absorbed onto silica gel and applied to the top of a silica gel column (10 cm×7 cm). The column was eluted with hexanes-Et₂O (1:1) to remove any unreacted materials and then with Et₂O to obtain the desired product mixed with the N-3 isomer. The ether elutant was then concentrated and cooled until the desired compound began to crystallize. In this manner 3.8 g (47%) of the desired compound was collected and identified by spectroscopy.

The mother liquor was then concentrated to several ml and applied to 20 thick layer silica gel plates. The plates were then developed in Et₂O-hexanes (2:1) (4×) until the desired compound separated from the slower moving N-3 isomer (55). The product bands were then eluted with ethyl acetate (Et OAc). The solvent was removed under reduced pressure. The resultant product has the structural formula:

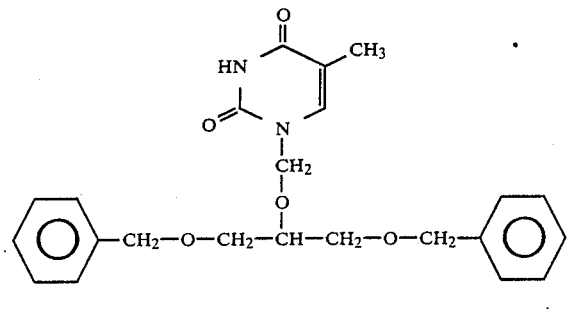

Dibenzyl-5-methyl U*

EXAMPLE 7

Preparation of 5-aza-1-[2-benzyloxymethyl[1-benzyloxy]methyl]cytosine

5-Azacytosine (5.0 g, 0.0446 mole) and some ammonium sulfate (100 mg) were suspended in HMDS (40 ml) and brought to reflux with stirring. After 20 minutes more ammonium sulfate was added and 20 minutes later the mixture became clear. The excess HMDS was evaporated under reduced pressure to yield a white solid, silyl-protected 5-azacytosine, which was used without further purification. The solid was dissolved in DCE (100 ml) and anhydrous stannic chloride (3.5 ml) was added. Then 1,3-dibenzyloxy-2-chloromethoxy propane (0.040 mole) was added and the solution was allowed to stand overnight at room temperature. The reaction solution was poured into aqueous bicarbonate, diluted with chloroform and shaken. The resultant precipitate was removed by filtration through celite. The phases were separated. The aqueous phase was extracted once with chloroform. The organic phases were combined, washed once with water, dried with anhydrous sodium sulfate and evaporated to yield 15 g of syrup. The syrup was dissolved in chloroform (20 ml) and applied to a tlc silica column (14.5×6.5 cm). The column was first eluted with chloroform (450 ml). The solvent was changed to 5% methanol in chloroform and the collection of fractions (10–15 ml) was begun. The desired compound 5-aza-1-[[2-benzyloxymethyl-[benzyloxy]-ethoxy]methyl]cytosine had was recovered from the appropriate fraction, analysed and shown to have the general formula:

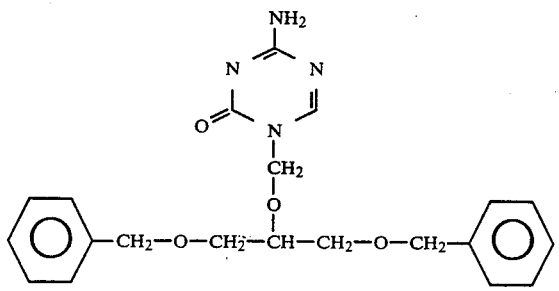

EXAMPLE 8

Preparation of 1-[[2-hydroxy-1-(hydroxy methyl)ethoxy]methyl]cytosine (C*)

Cytosine (5.0 g, 0.045 mole) was suspended in 1,1,1,3,3,3-hexamethyldisilazane (80 ml, 60 g HMDS) and several crystals of ammonium sulfate were added (modelled on: G. Ritzmann & W. Pfleiderer, Chem. Ber. 106, 1401 (1973)). The stirred mixture was protected from moisture and refluxed until a clear solution was obtained. If a clear solution was not obtained after one-half hour of reflux the addition of more ammonium sulfate gave a clear solution after another 10 minutes of reflux. The clear hot solution was connected to a water aspirator and the excess HMDS was carefully removed on a hot water bath to yield a white solid which was used in the next step without purification.

The 2,4-bis-(trimethylsilyl)cytosine was dissolved in dry DCE (200 ml) and stannic chloride (3.4 ml, 29.1 moles anhydrous freshly distilled) was added. Then 40 g of stock 1,3-dibenzyloxy-2-chloromethoxy propane solution (40 moles) was added and the yellow solution was allowed to stand overnight at room temperature.

The resultant product, 1-[[2-benzyloxy-1-(benzyloxymethyl)]ethoxymethyl]cytosine (5.59 g) was dissolved in warm ethanol (100 ml). Then 18 ml of wet (ethanol) palladium black was added with the aid of 80 ml of ethanol. Then 90 ml of cyclohexene was added. The stirred mixture was put under reflux for three hours when tlc showed that the reaction was complete. The mixture was filtered and the catalyst was washed with ethanol. The ethanol solution was evaporated under reduced pressure to yield a syrup and some crystals. The material was dissolved in 15 ml of hot methanol and seeded. The crystals were filtered and washed with methanol to yield 2.045 g of crystals. The mother liquor was concentrated, crystallized, and filtered several times to yield an additional 0.365 g of crystals.

The resultant compound, 1-[[2-hydroxy-1-(hydroxymethyl)ethoxy]methyl]cytosine, hereinafter referred to as C* has the structural formula:

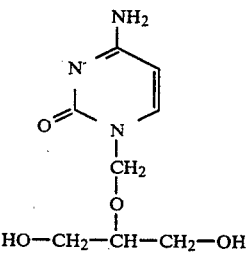

EXAMPLE 9

Compounds prepared according to the above examples were tested for activity against various types and strains of virus. Tests were carried out in vitro using plaque reduction methods. Titers of the virus strains in human fetal fibroblast cells were determined using the plaque titration method of Roizman & Roane ("Virology", 15, 75–79, 1961). Some virally infected cells are heated with the test compounds, and incubated, whilst other are left untreated as controls, and incubated. The reduction in number and size of plaques in the test plates, as compared with controls, is determined visually to detect anti-viral activity of the test compounds.

The compound of Example 1, namely dibenzyl-chloro-G* proved to have high activity against coxsackievious 3, a result confirmed by in vivo testing in mice.

The compound of Examples 2 and 3, namely G*, has previously been reported to be extremely active against herpes simplex virus types I and II.

The compounds of Example 4, namely iso-G* and monobenzyl-SFU* proved to be active against vesicular stomatitis (VSV).

The compound of Example 6, namely dibenzyl-5methyl-U* showed activity against both VSV and influenza virus A.

The compounds of Examples 7 and 8, namely 5-aza-dibenzyl-C*, and C* proved to be active against herpes simplex virus type I.

I claim:
1. The triazine compound 5-aza-1-[[2-benzyloxymethyl-[1-benzyloxy]-ethoxy]methyl]cytosine.

* * * * *